United States Patent [19]

Braginetz et al.

[11] Patent Number: 4,888,002
[45] Date of Patent: Dec. 19, 1989

[54] DISPOSABLE SHIELD MEDICAL SYRINGE

[76] Inventors: Paul A. Braginetz, 214 Oak Ridge Cir.; Mark R. Leadbetter, 1926 Spring Hill Rd.; Joseph Peduto, Rte. 5, all of Staunton, Va. 24401

[21] Appl. No.: 238,140
[22] Filed: Aug. 30, 1988
[51] Int. Cl.$^4$ ............................................. A61M 5/32
[52] U.S. Cl. .................................. 604/195; 604/218; 604/220
[58] Field of Search ............... 604/195, 196, 220, 187, 604/193, 194, 218

[56] References Cited

U.S. PATENT DOCUMENTS 4,507,117 3/1985 Vining et al. ...................... 604/196
4,710,170 12/1987 Haber et al. ....................... 604/195

FOREIGN PATENT DOCUMENTS 1287742 1/1969 Fed. Rep. of Germany ...... 604/220

Primary Examiner—John D. Yasko
Attorney, Agent, or Firm—Brady, O'Boyle & Gates

[57] ABSTRACT

A disposable shielded medical syringe wherein the contaminated needle is connected to a piston slidably mounted in the syringe barrel. The syringe plunger piston is threadably connectable to the needle piston for pulling the contaminated needle into the barrel to the shielded position. The syringe plunger is disconnectable from the plunger piston after the needle has been moved to the shielded position and a cap is insertable into the open end of the syringe barrel to completely enclose the contaminated needle.

9 Claims, 2 Drawing Sheets

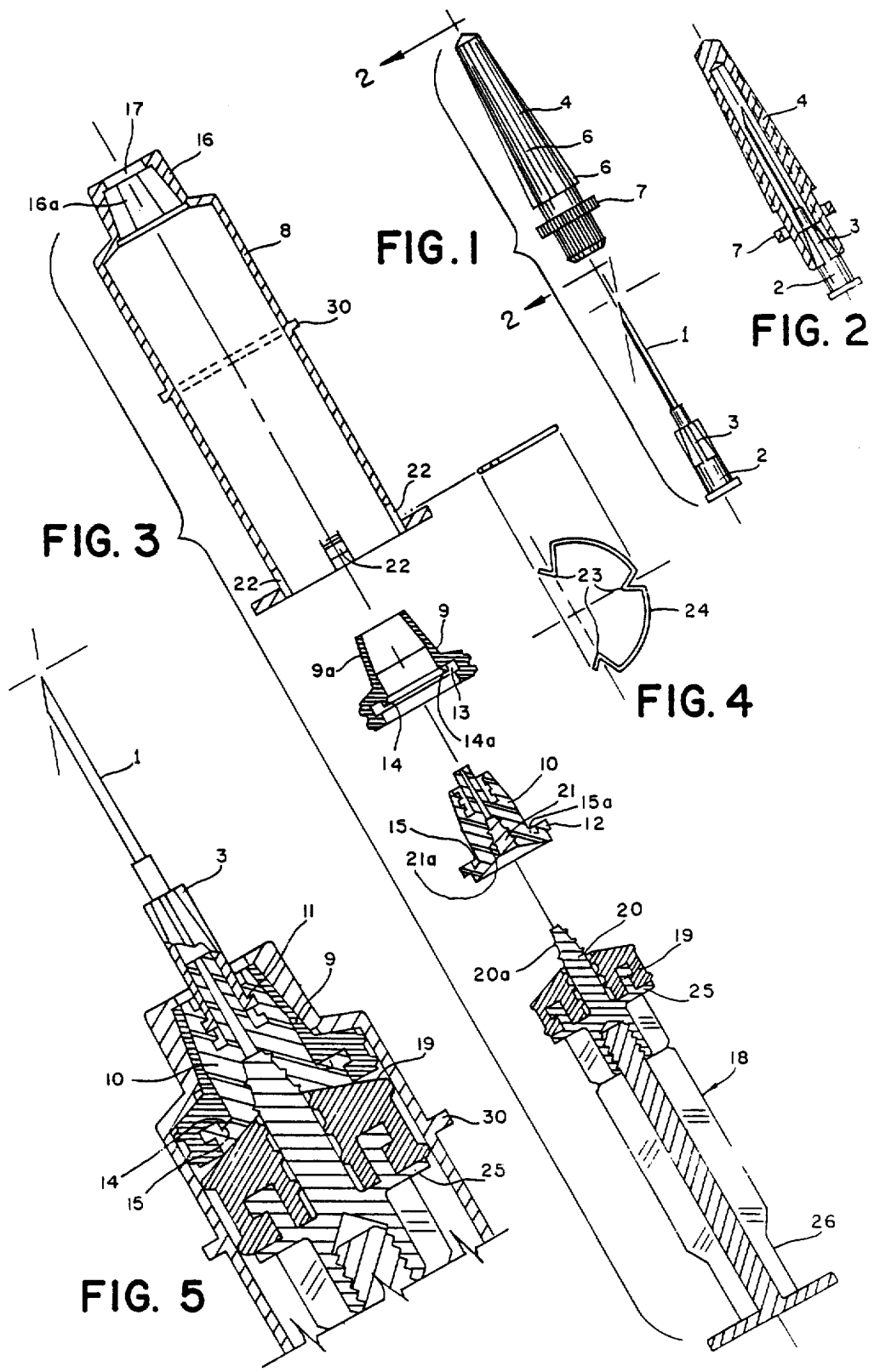

4,888,002

DISPOSABLE SHIELD MEDICAL SYRINGE

CROSS-REFERENCE TO RELATED APPLICATION

This application relates to a disposable shielded medical syringe of the type disclosed in applicants' copending application Ser. No. 07/232,775, filed Aug. 16, 1988 entitled DISPOSABLE SHIELDED MEDICAL SYRINGE.

BACKGROUND OF THE INVENTION

Medical personnel have to exercise the utmost of care when using conventional syringes so as not to be accidentally punctured by a contaminated syringe needle resulting in possible exposure to infectious diseases, such as acquired immune deficiency syndrome (AIDS) or serum hepatitis when injecting a medicament into a patient.

While various safeguards have been provided, such as protective caps for covering a used needle and sharps containers for the disposal of the used needle, it has been found that the chance of accidental puncture is most likely to occur during the manipulation of the syringe to either cap the needle or inverting the used needle into the sharps container.

In an effort to improve the safeguards for used syringe needles, it has been proposed to provide the syringe with a sleeve slidably mounted on the syringe barrel and movable from a retracted position on the syringe barrel to an extended position at the distal end of the barrel, to thereby provide a shield surrounding the used needle. The sleeve is releasably held in the retracted and extended positions by detents which are manually actuated by the user. These sleeve-type shields have not proven entirely satisfactory due, mainly, to the manual dexterity required by the user to release one detent for sliding the sleeve to the needle protecting position and then to actuate another detent for holding the sleeve in the extended position.

In order to overcome the disadvantages experienced in hitherto employed shielded medical syringes, the disposable shielded medical syringe of the present invention has been devised which comprises, essentially, a syringe barrel including a plunger threadably connected to a piston on the end thereof, the piston being slidably mounted in the barrel in sealing engagement with the barrel side wall. The syringe needle is connected to a second piston assembly slidably mounted with the barrel, in sealing engagement with the barrel side wall and located between the distal end of the barrel and the plunger piston. The plunger piston is adapted to be threadably connected to the needle piston assembly for withdrawing the contaminated needle into the syringe barrel. By this construction and arrangement, medicament is dispensed from the syringe by pushing the plunger toward the distal end of the barrel. After the medicament has been dispensed, the plunger is rotated to threadably couple the plunger piston to the needle piston assembly. The plunger is then pulled toward the proximate end of the barrel, thereby causing the contaminated needle and associated piston assembly to be withdrawn to a shielded position within the syringe barrel. The plunger is then disconnected from its piston and discarded, to thereby prevent the needle and associated piston assembly from being pushed once again toward the distal end of the barrel.

To complete the shielding of the used needle, a cap or scabbard is inserted into the distal end of the syringe barrel.

A spring clip is mounted on the proximate end portion of the syringe barrel providing a stop member to prevent the syringe plunger from being pulled completely out of the barrel.

BRIEF DESCRIPTION OF THE DRAWINGS

FIG. 1 is an exploded view of a syringe needle and cap or scabbard;

FIG. 2 is a sectional view of the cap taken along line 2—of FIG. 1 showing the cap mounted on the needle;

FIG. 3 is an exploded view of the syringe of the present invention without the needle and cap assembly illustrated in FIGS. 1 and 2:

FIG. 4 is a plan view of a spring clip employed as a stop member in the syringe barrel to prevent complete withdrawal of the syringe plunger from the barrel;

FIG. 5 is an enlarged fragmentary, sectional view of the syringe taken along line 5—5 of FIG. 6;

DESCRIPTION OF THE PREFERRED EMBODIMENT

Figure 6:
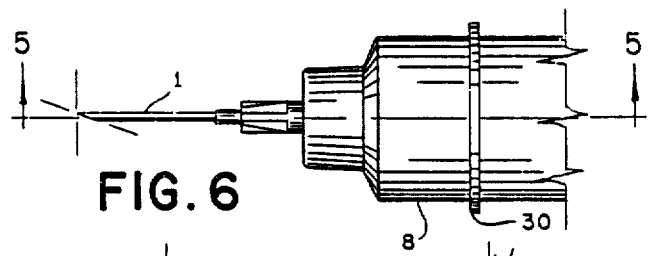
FIG. 6 is a fragmentary top plan view showing the distal end portion of the syringe barrel and associated needle.

Referring to the drawings and more particularly to FIGS. 1 and 2, a conventional syringe needle 1 is shown having a Luer Lock hub portion 2 having lands 3. The needle is provided with a cap or cover 4 slidably mounted on the hub portion 2 of the needle, the lands 3 of the needle hub being engageable with a rib integral with the interior wall of the cap 4. The exterior wall of the cap 4 is provided with integral lands 6 and a flange portion 7.

FIGS. 3 and 5 illustrate the components of the syringe assembly of the present invention to which the syringe needle 1 and associated cap 4 of FIGS. 1 and 2 are adapted to be connected. The syringe assembly comprises a cylinder or barrel 8 having a hollow piston 9 slidably mounted therein in sealing engagement with the interior wall of the barrel. The piston 9 carries a Luer Lock member 10 into which the needle hub portion 2 is threadably secured as at 11. The member 10 ils provided with an annular flange 12 which is received within a similarly configured groove 13 provided in the end portion of the piston 9, to thereby sealably secure the Luer Lock member 10 within the piston 9. To prevent rotation of the Luer Lock member 10 relative to the piston 9 during the connection of the needle 1 thereto, the piston 9 is provided with an annular rim 14 extending into a similarly configured recess 15 provided in the oppositely extending face of the Luer Lock member 10. The annular rim is interrupted as at 14a to provide a radially extending recess for receiving a radially extending rib 15a provided in the recess 15. The piston 9 tapers inwardly and is provided with a polygonal outer surface 9a conforming to a conical portion 16 on the distal end of the cylinder 8 having a polygonal inner surface 16a. By this construction and arrangement, the mating or cooperating polygonal surfaces 9a and 16a prevent rotation of the piston 9 when coupling the plunger piston thereto, to be described more fully hereinafter. The conical portion 16 of the barrel 8 is also provided with an opening 17 on the end thereof through which the needle 1 and hub 2 extend when connected to the Luer Lock member 10, as shown in FIG. 5.

To complete the structure of the syringe assembly of the present invention, a plunger 18 having a piston 19 on the end thereof is slidably mounted within the proximate end portion of the barrel 8, the piston 19 having a projection 20 extending axially therefrom and provided with threads 20a receivable within a similarly configured aperture 21 in the Luer Lock member 10, having a cooperating thread portion 21a, whereby the plunger piston 19 can be threadably connected to the syringe needle piston assembly.

Figure 10:
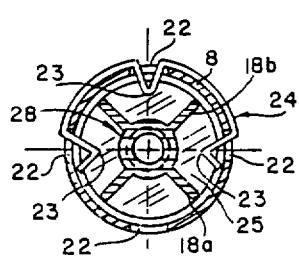
FIG. 10 is a view taken along line 10—10 of FIG. 9.

As will be seen in FIGS. 3 and 10, the proximate end portion of the barrel wall is provided with a plurality of apertures 22 for receiving inwardly extending finger portions 23 carried by a spring clip 24 mounted on the exterior surface of the barrel wall, whereby the spring clip fingers 23 are adapted to engage the plunger flange 25 adjacent the piston 19, to thereby prevent complete withdrawal of the plunger 18 from the barrel 8.

Figure 8:
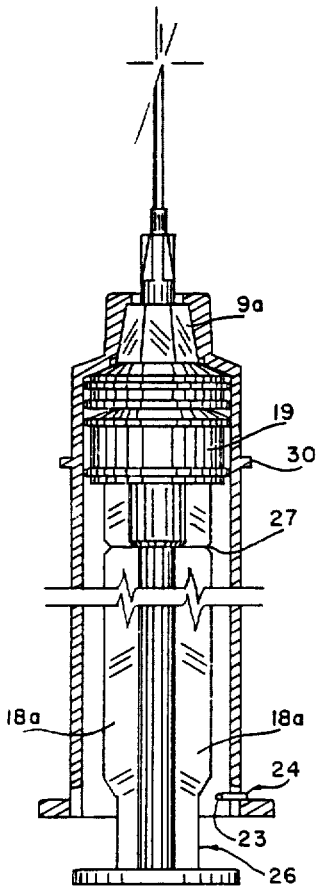
FIG. 8 is a sectional view of the relative positions of the plunger piston and needle piston assembly during the coupling of the pistons to each other.

Referring to FIGS. 8 and 10, it will be seen that the plunger 18 is cruciform in cross-section having radially extending arm portions 18a, 18b. At the proximate end portion of the plunger 18, the radial dimension of the arm portions is reduced as at 26, whereby the finger portions 23 of the spring clip 24 are precluded from preventing rotation of the plunger 18 when connecting the plunger piston 19 to the Luer Lock member 10 and associated piston 9.

Figure 9:
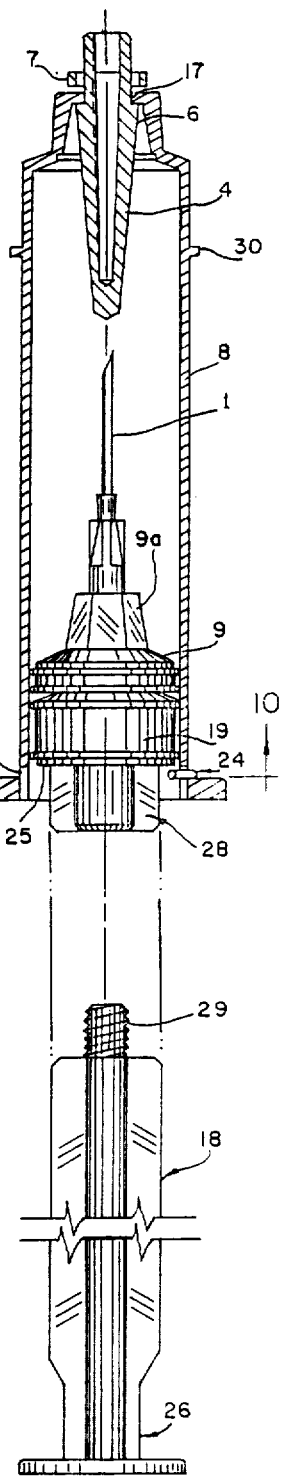
FIG. 9 is a sectional view of the needle piston assembly and plunger piston moved to the shielded position within the syringe barrel with the plunger disconnected therefrom, and the cap inserted into the open end of the barrel.

To further enhance the disposability of the shielded medical syringe of the present invention, the distal end portion of the plunger 18 is interrupted as at 27 and the hub portion 28, FIG. 10, is provided with internal threads adapted to receive a threaded stem 29 on the end of the plunger 18, whereby, after the needle 1 and associated piston have been pulled to the shielded position as shown in FIG. 9, the plunger 18 is rotated, to thereby disconnect the plunger 18 from the piston 19. When in the retracted position, the spring fingers 23 will abut the side faces of the arms 18a and 18b to prevent the piston 19 from rotating while the plunger 18 is being disconnected therefrom.

The contaminated needle 1 is completely enclosed by inserting the cap 4 in an upside-down manner through the barrel opening 17. The cap flange 7 prevents the cap from being inserted completely into the barrel 8 and the ends of the cap lands 6 engage the portion of the end wall of the distal end of the barrel surrounding the aperture 17. To facilitate the insertion of the cap 4 through the barrel opening 17, the cap lands 6 can be resilient so that they can be squeezed or compressed while being inserted through the opening, or alternatively, if the lands 6 are rigid, the portion of the end wall of the distal end of the barrel surrounding the aperture 17 can be made resilient, to thereby expand during the insertion of the cap 4.

Figure 7:
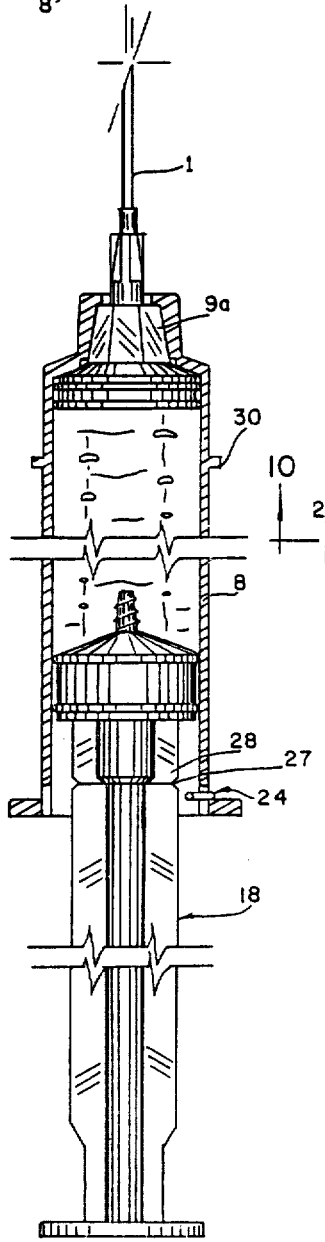
FIG. 7 is a sectional view illustrating the relative positions of the plunger piston and needle piston assembly when dispensing medicament from the syringe.

In the operation of the disposable shielded medical syringe of the present invention, the medicament is dispensed from the barrel 8 through the Luer Lock member 10 and needle 1 by pushing the plunger 18 inwardly of the barrel as shown in FIG. 7. After the medicament has been dispensed from the syringe, the medical person will wrap one hand around the barrel 8 remote from the contaminated needle 1 behind the finger protecting flange 30 provided on the exterior surface of the barrel, and with the other hand rotate the plunger 18, to thereby threadably couple the plunger piston 19 to the Luer Lock member 10 and associated piston 9. The plunger 18 and associated pistons 9 and 19 are then pulled inwardly of the syringe barrel 8, as shown in FIG. 9. The plunger 18 is then disconnected from the piston 19 and discarded, and the cap 4 is inserted into the barrel opening 17 as described hereinabove. By disconnecting the plunger 18 from the piston 19, the contaminated needle 1 cannot be inadvertently pushed in the opposite direction through the barrel opening 17 in the event that the cap 4 has not been placed thereon.

From the above description, it will be readily apparent to those skilled in the art that the disposable shielded medical syringe of the present invention provides an improved disposable shielded syringe needle requiring minimal manipulation to move the contaminated needle to the shielded position, and by providing the feature of disconnecting the plunger from the plunger piston, together with the placement of the cap on the open end of the barrel, there is provided an improved safeguard for medical personnel against exposure to infectious diseases.

It is to be understood that the form of the invention herewith shown and described is to be taken as a preferred example of the same, and that various changes in the shape, size and arrangement of parts may be resorted to, without departing from the spirit of the invention or scope of the subjoined claims.

We claim:

1. A disposable shielded medical syringe comprising a syringe barrel, a plunger slidably mounted in said barrel, a piston secured to the distal end of the plunger and being in sealing, sliding engagement with the inner wall of the barrel, a second piston slidably mounted in said barrel and being in sealing, sliding engagement with the inner wall of the barrel and being positioned between the distal end portion of the barrel and the plunger piston, a syringe needle extending outwardly longitudinally of the barrel at the distal end thereof, means for detachably connecting the syringe needle to said second piston, means for mechanically connecting said plunger piston to said means for connecting the syringe needle to said second piston, said second piston having a configured outer surface cooperating with a similarly configured inner surface on the distal end of said barrel, to thereby prevent the second piston from rotating within the barrel when the needle is being operatively connected thereto and also preventing the second piston from rotating within the barrel when the plunger piston is being operatively connected thereto, and a medicament contained within the barrel between the plunger piston and the second piston, whereby the medicament is dispensed through the needle by pushing the plunger inwardly, whereupon the plunger piston is mechanically connected to the means for connecting the syringe needle to said second piston, and the second piston and associated contaminated needle is drawn inwardly to a shielded position within the barrel by pulling the plunger in a direction toward the proximate end of the barrel.

2. A disposable shielded medical syringe according to claim 1, wherein the means for connecting the syringe needle to the second piston comprises, a Luer Lock member operatively connected to said second piston, said needle having a Luer Lock hub portion, said needle Luer Lock hub portion being threadably connected to said Luer Lock member.

3. A disposable shielded medical syringe according to claim 2, wherein the means for mechanically connecting the plunger piston to the Luer Lock member comprises a threaded projection extending axially from the plunger piston, and a similarly configured threaded aperture provided in said Luer Lock member.

4. A disposable shielded medical syringe according to claim 1, wherein a needle cap is insertable into the open end of the barrel to prevent the contaminated needle from being moved from the retracted, shielded position outwardly through the open end of the barrel.

5. A disposable shielded medical syringe according to claim 1, wherein spring stop means are mounted on the proximate end portion of the barrel adapted to be engaged by the syringe piston when fully retracted to thereby prevent complete removal of the syringe piston from the barrel.

6. A disposable shielded medical syringe according to claim 1, wherein connecting means are provided between the plunger and plunger piston, whereby the plunger is disconnected from the plunger piston after the contaminated needle is moved to the shielded position.

7. A disposable shielded medical syringe comprising a syringe barrel, a plunger slidably mounted in said barrel, a piston secured to the distal end of the plunger and being in sealing sliding engagement with the inner wall of the barrel, a second piston slidably mounted in said barrel and being in sealing, sliding engagement with the inner wall of the barrel and being positioned between the distal end portion of the barrel and the plunger piston, a syringe needle extending outwardly longitudinally of the barrel at the distal end thereof, means for connecting the syringe needle to said second piston, means for mechanically connecting said plunger piston to said means for connecting the syringe needle to said second piston, and a medicament contained within the barrel between the plunger piston and the second piston, said second piston having a polygonal outer surface, the distal end portion of the barrel having a polygonal inner surface cooperating with the polygonal outer surface on the second piston, whereby the second piston is prevented from rotating within the barrel when the needle is being operatively connected to said second piston.

8. A disposable shielded medical syringe of the type wherein the syringe needle is retracted into the syringe barrel through the open end of the barrel, the improvement comprising spring stop means mounted on the proximate end portion of the barrel adapted to be engaged by the syringe piston when fully retracted to thereby prevent complete removal of the syringe from the barrel, the syringe piston including a plunger having a threaded stem portion threadably mounted in a threaded hub portion on the piston whereby the plunger can be disconnected from the piston when the piston has been moved to the retracted position, radially extending arms on said hub portion, portions of the spring stop means being engageable with said arms to thereby prevent rotation of the piston during the disconnecting of the plunger therefrom.

9. A disposable shielded medical syringe comprising a syringe barrel, a plunger slidably mounted in said barrel, a piston secured to the distal end of the plunger and being in sealing sliding engagement with the inner wall of the barrel, a second piston slidably mounted in said barrel and being in sealing, sliding engagement with the inner wall of the barrel and being positioned between the distal end of the barrel and the plunger piston, a syringe needle extending outwardly of the barrel at the distal end thereof, means for connecting the syringe needle to said second piston, and a medicament contained within the barrel between the plunger piston and the second piston, said second piston having a polygonal outer surface, the distal end portion of the barrel having a polygonal inner surface cooperating with the polygonal outer surface on the second piston, whereby the second piston is prevented from rotating within the barrel when the needle is being operatively connected to said second piston.

* * * * *